(12) United States Patent
Loucks et al.

(10) Patent No.: US 7,114,376 B2
(45) Date of Patent: Oct. 3, 2006

(54) BALE LOADER MOISTURE SENSING SYSTEM

(76) Inventors: Levi L. Loucks, 8570 U.S. Hwy. 95, Marsing, ID (US) 83639; Lamon Loucks, 8570 U.S. Hwy. 95, Marsing, ID (US) 83639

( * ) Notice: Subject to any disclaimer, the term of this patent is extended or adjusted under 35 U.S.C. 154(b) by 121 days.

(21) Appl. No.: 10/776,552

(22) Filed: Feb. 10, 2004

(65) Prior Publication Data
US 2005/0172701 A1    Aug. 11, 2005

(51) Int. Cl.
*G01N 27/12* (2006.01)
(52) U.S. Cl. .......................... 73/73; 414/24.5
(58) Field of Classification Search ............ 73/73, 73/866, 865.8; 414/24.5, 25, 721, 111, 789.7; 294/107, 120, 122, 123; 324/664–670, 694–696
See application file for complete search history.

(56) References Cited

U.S. PATENT DOCUMENTS

| | | |
|---|---|---|
| 4,451,781 A | 5/1984 | Anderson |
| 4,812,741 A | 3/1989 | Stowell |
| 4,868,491 A | 9/1989 | Black |
| 4,911,596 A * | 3/1990 | Fetter ................. 414/24.5 |
| 4,929,904 A * | 5/1990 | Bohman et al. ........... 324/696 |
| 5,150,999 A * | 9/1992 | Dugan ................. 414/24.5 |
| 5,184,077 A | 2/1993 | Day et al. |
| 5,514,973 A | 5/1996 | Byler et al. |
| 5,758,479 A | 6/1998 | Staheli |
| 6,020,744 A | 2/2000 | Ghorashi et al. |
| 6,088,657 A | 7/2000 | McMahon |
| 6,121,782 A | 9/2000 | Adams et al. |
| 6,242,927 B1 | 6/2001 | Adams et al. |
| 6,377,058 B1 | 4/2002 | Pemrick |
| 6,489,784 B1 | 12/2002 | Adams et al. |
| 6,526,731 B1 | 3/2003 | Hunter et al. |

\* cited by examiner

*Primary Examiner*—Robert Raevis
(74) *Attorney, Agent, or Firm*—Robert L. Shaver; Dykas, Shaver & Nipper, LLP

(57) ABSTRACT

A moisture sensing system for use with a bale loading vehicle. The moisture sensing system includes one or more probes that are inserted into the center of a hay bale or other agricultural product that obtain moisture readings of the product. The moisture readings are stored in memory, and may be printed in a report of moistures over a certain period of time, in a certain location, in a certain lot number, in a certain truckload, or other grouping of bales.

13 Claims, 2 Drawing Sheets

BALE LOADER MOISTURE SENSING SYSTEM

BACKGROUND OF THE INVENTION

1. Field of the Invention

The present invention generally relates to moisture sensors, and more particularly relates to moisture sensors mounted on vehicles for moving agricultural products.

2. Background Information

Agricultural products such as hay, alfalfa, grass, straw, cotton, and other fibrous materials are packed into bales of various shapes during part of their processing. The bales can be large cylindrical bales, small rectangular bales, or large rectangular bales. These agricultural products will be referred to as hay bales, but may include any type of baled agricultural product. The bales are typically stacked either side-by-side or in a multi-layer configuration. The bales may be covered by plastic or placed under a covering or left out in the open. The moisture content of the agricultural product can be a problem with such baled products. If the moisture content is too high, the wet areas of the bale can produce heat, and the heat can be sufficient to start a fire therein. When a bale catches fire, it can cause neighboring bales to catch fire and the entire haystack, along with the barn or shed it is in, can be destroyed by fire. This is a problem for people who grow such agricultural products, transport, store, buy, and insure them.

Such fires usually occur within six weeks of baling, but may occur in hay several years old. Fire can occur in loose hay and all types of bales or stacks. Fires can occur in hay stored inside or outside. The fires are caused by the growth of microorganisms in the hay. As a microorganism feeds and multiplies, they generate heat. If the moisture content of the hay is high enough, this allows the microorganisms to grow. If the moisture content is in the center of the bale, then heat begins to be produced, which is slow to dissipate from the center of a large bale. Certain bacteria grow well in hot conditions. These are called thermophilic (heat loving) bacteria. When microorganisms cause an elevated temperature, the presence of thermophilic bacteria allows them to begin growing in the more intense temperatures and they can then boost temperatures to a higher level. At these higher temperatures, carbon in the hay combines readily with oxygen and the heated hay can self ignite in the presence of air. This process causes spontaneous combustion of the hay.

Therefore, it is important to know the moisture content of the hay, especially in the center. There are numerous moisture sensors in the prior art, such as moisture probes that are inserted by hand into a hay bale, or which are mounted on the hay baler itself. The hay baler mounted moisture sensors have a sensor on the side of a chute down which the hay bale travels. As the hay bale travels down the chute, the moisture sensor determines the moisture of the hay on the exterior of the bale. However, it does not sense the moisture of the hay in the interior of the bale. After baling, the bale may gradually dry over a period of time.

One step in the operation that would make the most difference in preventing hay fires is the step of loading, transporting, or stacking hay bales. If at this step the moisture content in the interior of a hay bale could be sensed, bales that have moist centers could be segregated and dealt with. This would have the advantage of eliminating hay fires and thus eliminating the loss of the agricultural product as well as the barn or structure that it is enclosed within.

This would also be of benefit to insurance companies. If the insurance company knew the moisture content of a group of bales, the insurance company could insure the agricultural product at a lower price, thus saving the grower money in premiums.

The ideal time to take the moisture sensing step is when a bale loading vehicle is moving the bale from one place to another, as the bales are loaded into a truck, stacked in a barn, or moved from the field to a shed. In addition to sensing the moisture while a bale is being moved, such a moisture sensing vehicle could test the moisture of bales merely by driving up to the bale and taking a moisture reading.

What is missing in the prior art and therefore what is needed, is a moisture sensing system that is operated in conjunction with a bale lifting vehicle. Such a moisture sensing system would be able to sense the moisture of an interior of a hay bale, preferably at more than one point. It would also have a moisture readout that is visible to the vehicle's operator, so that moisture readings could be taken and evaluated without the operator leaving the seat of the vehicle. Ideally such a system would have a way to record moisture and enter information about bale numbers, lot numbers, bale locations, barn numbers, and other information related to identifying such bales. Such a device would also have the ability to store such information in memory, and print it out when a report was necessary. The report could be utilized by the farmer to obtain better insurance rates, by the shipper to know that the shipping container would not be destroyed by fire, by transporters to ensure that their equipment is not at risk by fire, and by the grower to verify that the hay is not in danger of burning. They hay purchaser would also benefit by this report, whether generated by the farmer or by the purchaser.

SUMMARY OF THE INVENTION

These and other objects are accomplished by the moisture sensing system of the present invention. This system is for use on bale lifting vehicles such as front-end loaders, tractors, pickup trucks, forklifts, and other vehicles that are configured for lifting hay bales. Each of these vehicles can be outfitted with bale lifting equipment such as spears, forks or clamps, by which these vehicles can lift and move a bale of hay. The moisture sensing system includes one or more bale penetrating rods mounted to the vehicle or to the bale lifting attachment of the vehicle. A bale penetrating rod is for insertion into a bale of product in order to test the moisture of the product in the interior of the bale or stack. The system also includes one or moisture sensing probes, which are attached to the bale penetrating rods. Each probe includes electrodes that are spaced apart from each other so that electrical current between the electrodes can be utilized to determine the moisture content in the bale.

The product that can be tested in the moisture sensing system can be any type of agricultural product, such as hay, alfalfa, hay, grass, straw, cotton, and any other fibrous product. The system includes a sensor readout that is mounted on the vehicle in a position that is visible to the vehicle's operator. The system is designed to penetrate the bale with the bale penetrating probes, and take a moisture reading when the bale lifting vehicle moves adjacent a bale. Once adjacent a bale and with the bale penetrating probe inside the bale, the driver of the vehicle can read the moisture content of the bale from inside the vehicle. Once the moisture is sensed, the bale would typically be lifted and transported to another location. However, transportation of the bale is not required, and the moisture can be sensed on a bale without moving it.

The device can utilize the spears or rods of a bale lifting vehicle to serve as the bale penetrating rods of the sensor. In that case, the moisture sensing probe would be attached to the rods or spears that are used by the vehicle to lift and/or move bales. The preferred arrangement for moisture sensing is for the moisture sensing probes to sense the moisture in the approximate center of the bale of hay. If more than one moisture sensing probe is present in a particular configuration of the system, a number of positions in the hay bale are sensed for moisture and the readings may be displayed either as an average, or showing the individual moisture readings.

One desirable configuration of the system is to have moisture sensing probes that are capable of sensing the moisture of the bale as the probe is inserted into the bale. In this way, each probe would give a moisture reading of the path of insertion into the bale. Once again, these individual moisture readouts could be displayed as an average for that particular path of insertion or as discrete readings as the probe enters the bale.

The system can also include a moisture alert set point. A user would select a certain moisture percentage that would indicate a problem with a bale. Once the alert set point has been specified, if any moisture readings exceed that set point, a signal notifies a user that the alert set point has been reached or exceeded. The signal could be a visual alarm, such as a flashing red light, or it could be an audible tone such as a buzzer or alarm, or it could be a combination of both visual and audible alarms.

One embodiment of the moisture sensing system includes a memory storage device, such as computer with RAM memory. Moisture readings of bales can be recorded in the computer memory for later use. This version of the device would also include a printing device for printing out moisture content information of bales that have been sampled. One option with this variation of the device is to print a report of the moisture content of a selected lot of bales. In this way, a farmer would present the report of moisture of hay bales to an insurance company in order to receive lower premiums for coverage of the hay bales in that group. Other groupings of moisture readings could be provided, such as a report with the moisture of hay bales for an entire day, the moisture of hay bales in a certain lot, or the moisture of hay bales in a certain location. Each of these reports would be of value to the farmer and the insurance company. An information input device would also be an optional feature of such a system, so that the driver could input information about bale numbers, lot numbers, stack numbers, building names and numbers, date and time, and other information about the hay bales being sampled.

Further, the purpose of the foregoing abstract is to enable the United States Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measure by the claims, nor is it intended to be limiting as to the scope of the invention in any way.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive in nature.

DESCRIPTION OF THE PREFERRED EMBODIMENTS

Figure 1:
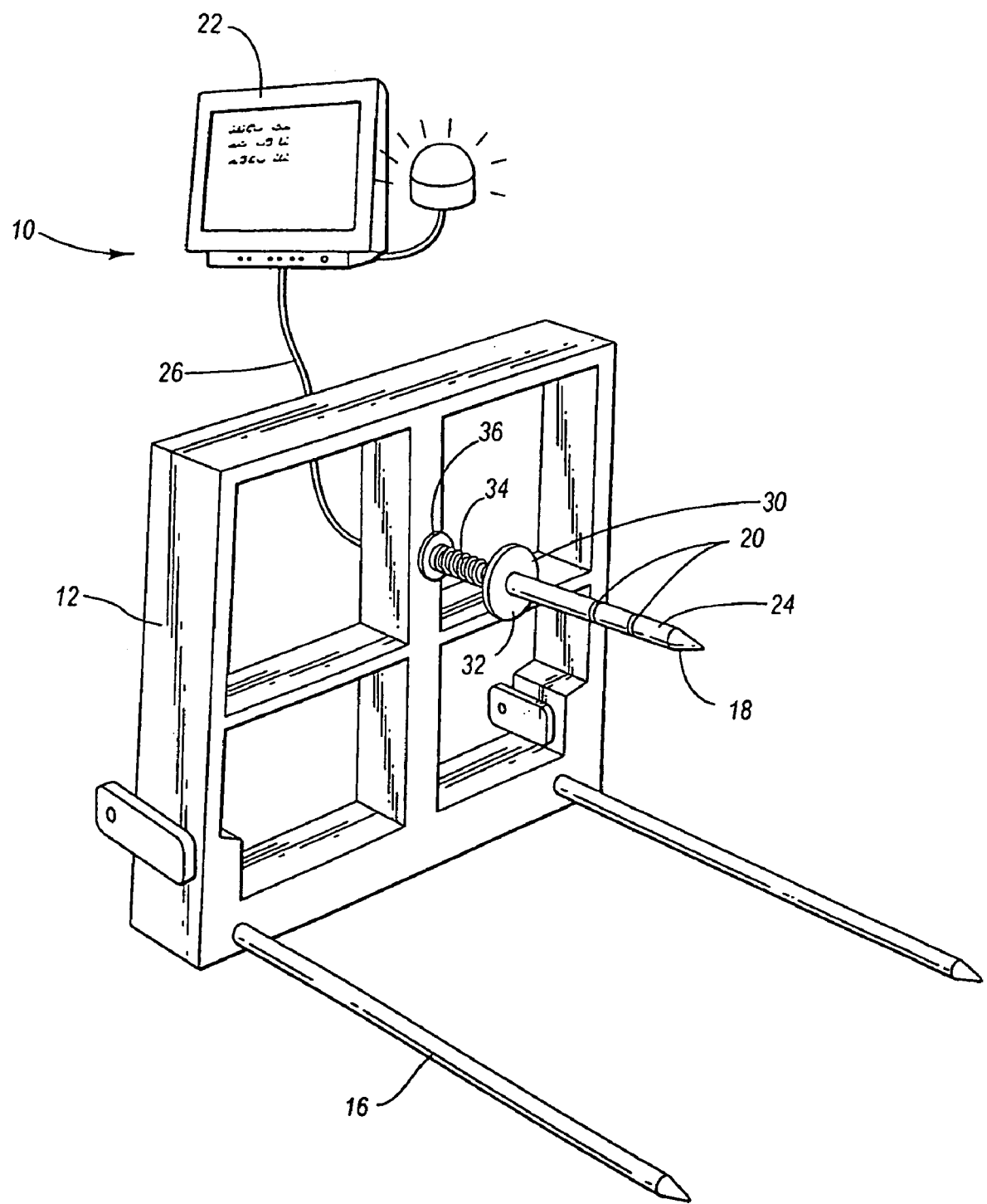
FIG. 1 is a perspective drawing of the moisture sensing system of the present invention.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

While the present invention is described with hay bales, it is to be distinctly understood that any agricultural product that is processed into variously shaped and sized bales can be utilized with the present invention.

Figure 2:
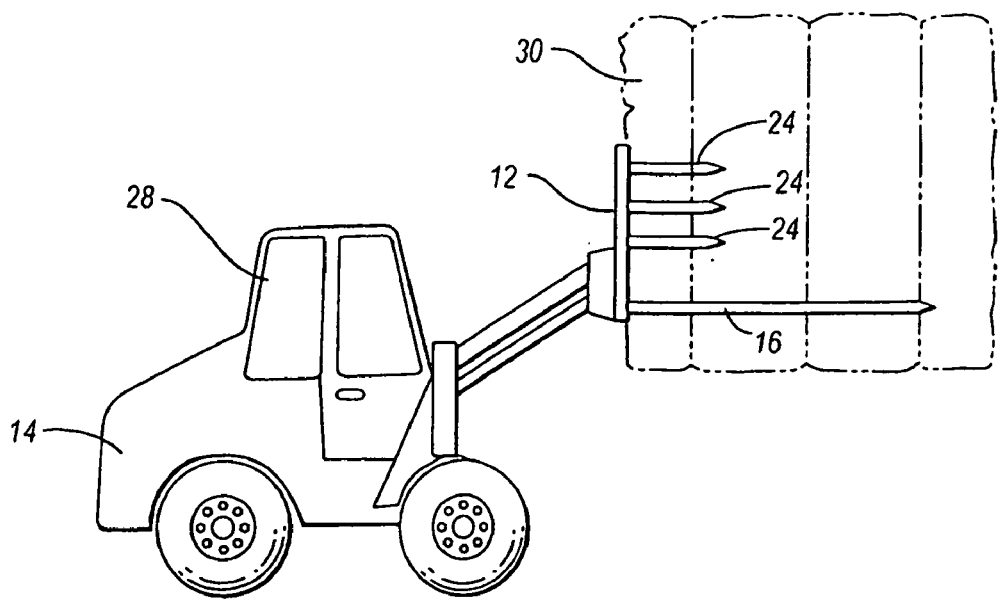
FIG. 2 is a side view of the moisture sensing system in use with a bale and a loader.
Figure 3:
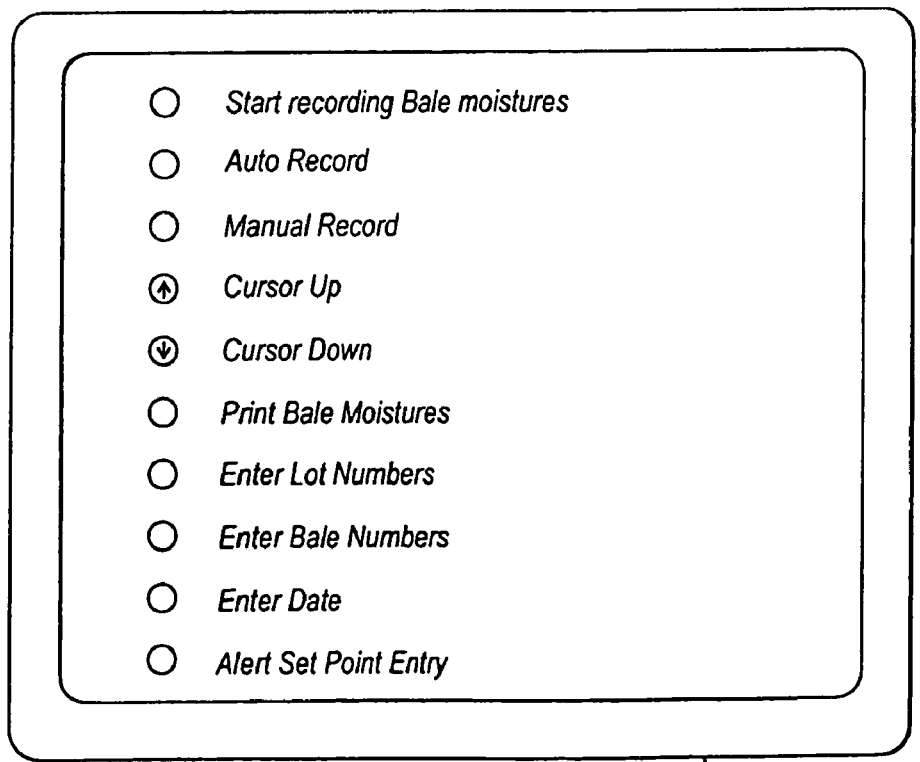
FIG. 3 is a view of a computer screen with features of a recording system of the present invention.

Several preferred embodiments of the present invention are shown to advantage in FIGS. 1–3. FIG. 1 shows one version of a moisture sensing system 10 mounted on a bale fork 12. The bale fork 12 would typically be mounted on a loader 14 as shown in FIG. 2. The moisture sensing system 10 is incorporated into the bale fork 12, and can take a number of different forms and be mounted on a number of different vehicles. For instance, bale forks can have a large number of configurations with different numbers of bale spears 16. Some bale lifting devices are clamps that clamp around the outside of a bale similar to giant tongs. The moisture sensing system of the present invention can also work with clamp type bale lifters. Other types of bale forks include bales forks that have curved hooks that rotate and engage a bale. The moisture sensing system of the present invention also works with this type of system or any other type of hay lifting system.

Shown in FIG. 2 is a loader, which is one typical way to lift large bales. Other vehicles can also be utilized with a variety of bale forks, including tractors, forklifts, and even pickup trucks.

The moisture sensing system of the present invention includes a bale penetrating rod 18. On the bale penetrating rod 18 are a pair of spaced apart electrodes 20, which together form a moisture sensing probe. A sensor readout 22 is operatively connected to the moisture sensing probe 24. Although this is shown in FIG. 1 by use of a wire connection 26, wireless technology could also be utilized to transmit a signal from the moisture sensing probe 24 to the sensor readout 22. The sensor readout 22 is configured to be mounted in a cab 28 of the vehicle so that the operator may read it as he/she pushes the bale fork 12 into a bale of hay 30. Associated with the sensor readout 22 of a preferred embodiment of the present invention is an alarm that can could be a flashing light, a light of a certain color, a sound generating device, or a combination of light and sound. The alarm sounds when a moisture reading is taken that exceeds an alert set point.

The preferred embodiment of the present invention includes an alert set point that may be specified by the operator. For instance, if it is determined that the alert set point of the day is to be 15% moisture, the drive would enter 15% moisture into the memory of the computing device associated with sensory readout 22. Thereafter, when any bales were sensed with a moisture higher than 15%, the alarm would go off alerting the operator that a higher than acceptable moisture reading had been taken.

The moisture sensing system preferably includes a computer with memory, in which the alert set point is recorded, and in which moisture readings of hay bales are also recorded. The memory is preferably configurable so that moisture readings may be grouped according to date, bale lot number, barn number, etc. In this way, moisture information that has been taken during a certain period of time or in a certain building may be grouped together and printed out in a report. This serves as quality control for the producer, as well as for the shipper or purchaser, who does not want to purchase hay bales with high moisture content. This also is a reassurance to an insurer, who might be able to provide lower rates for hay bales that have been tested and recorded. This is an advantage to the grower or person storing the hay bales because he/she can obtainer cheaper insurance rates.

The computer is associated with the sensor readout 22 and can take many forms. It can be in the form of a PDA, which is configured to receive moisture data from the moisture sensing probe 24 and record it using its software. It can also be a device that utilizes removable memory, such as a memory chip, disk, or CD, on which information can be recorded and removed from the vehicle to be placed in storage or further processed at a later date. It is also possible that a computing device would be configured to print out reports in the bale loading vehicle itself.

The computing means of the moisture sensing system will have a number of features, including input of data, including date, time, bale number, lot number, truck number, building number, farm name and number, and other information that will identify the sample bale. It will also have the ability to input and store measured moisture readings. When the moisture probe is inserted into a hay bale, a moisture reading is taken either when the sensor reaches equilibrium, or as the sensor is being pushed into the hay bale. In either case, a moisture value is recorded. The recording of the moisture value can be performed automatically, or it can include a manual input button, such as a button on a touch screen or a computer face, which would cause the sensed moisture to be recorded. One embodiment of this system can include an automatic moisture reading trigger 30, which is a mechanical device that is tripped every time a hay bale is loaded on the bale fork 12. This device is shown in FIG. 1 as a bale sensing disk 32, a spring 34, and a contact 36. When the bale fork is fully pressed into a bale, the bale sensing disk 32 is pressed toward the frame of the bale fork 12. In doing so, the spring 34 is compressed and eventually the bale sense disk 32 touches the contact 36, which initiates the recording of a moisture reading. In this way, every time a bale is loaded onto the bale fork 12, a moisture reading would be initiated and recorded.

Another preferred embodiment of the device includes a manual entry of the moisture reading. This could be performed by the operator pressing an entry button when the reading is taken, which enters the value at that time into memory. The entry button could be on a touch screen or on the face of the computer or a button accessible to the driver inside the cab.

FIG. 1 shows a bale fork utilizing two bale spears 16. Also shown is one bale penetrating rod 18. Another preferred embodiment of the present invention utilizes a number of bale sensing probes. FIG. 2 shows an embodiment of the present invention in which multiple moisture sensing probes 24 are utilized.

The moisture sensing system can also be utilized on bale forks by modifying the existing bale spears 16. For instance, a portion of the bale spears 16 could be cut off and replaced with a moisture sensing probe 24. In this way, a bale fork that had five bale spears 16, could be modified to include one or more moisture sensing probes 24 to be attached to the tip of the bale spears 16. When utilized with a system of multiple moisture sensing probes 24, the computer would have the capability of recording all of the moistures, the moistures along the path of probe insertion, and the average of the moisture readings, whichever is preferred by the operator.

FIG. 3 shows one possible configuration of the options available in the computer 38. These include a button to enter information, to begin recording bale moistures, to choose either auto or manual record mode, to enter lot numbers, bale numbers, dates, and alert set point, to move a cursor up, down, left, or right, or to print bale moistures. Each of these features could be displayed in a PDA, laptop computer, or other computing means, including a cellular telephone, a desktop computer linked to the moisture sensing system 10, or other computing means as they become available with the development of this technology.

While there is shown and described the present preferred embodiment of the invention, it is to be distinctly understood that this invention is not limited thereto but may be variously embodied to practice within the scope of the following claims.

From the foregoing description, it will be apparent that various changes may be made without departing from the spirit and scope of the invention as defined by the following claims.

We claim:

1. A moisture sensing system for use on a bale lifting vehicle, comprising:
   one or more bale penetrating rods mounted to said bale lifting vehicle, for insertion into a bale of product;
   one or more moisture sensing probes, attached to said one or more bale penetrating rods, each one or more moisture sensing probes with spaced apart electrodes for moisture sensing contact with a product in bale form;
   a sensor readout mounted on said vehicle in a position visible to a vehicle driver;
   wherein said one or more bale penetrating rods penetrate said bale and take a moisture reading when said bale lifting vehicle moves adjacent a bale, and the vehicle driver of said bale lifting vehicle can read the moisture of said bale while driving said vehicle.

2. The moisture sensing system of claim 1 in which said one or more moisture sensing probes are configured for retrofit mounting on bale penetrating rods of said bale lifting vehicle for use with the moisture sensing system.

3. The moisture sensing system of claim 1 in which said one or more moisture sensing probes are configured to test the moisture in the center of the bale of product.

4. The moisture sensing system of claim 1 in which one or more moisture sensing probes are capable of sensing moisture as the probe is inserted into the bale, and give one or more moisture readings of the path of insertion of the probe.

5. The moisture sensing system of claim 1 which includes a plurality of said moisture sensing probes and a moisture indicator which displays an average of the readings of said plurality of moisture sensing probes.

6. The moisture sensing system of claim 1 which includes an alert set point, and an alarm, wherein a user may select a specific moisture content as the alert set point, and if any moisture readings exceed the alert set point, a signal notifies the user that the alert set point has been exceeded.

7. The moisture sensing system of claim 6 in which said alarm is a visual alarm.

8. The moisture sensing system of claim 6 in which said alarm is an audio alarm.

9. The moisture sensing system of claim 1 which includes a memory storage device operatively connected to said one or more moisture sensing probes for recording moisture readings of bales of product for later use.

10. The moisture sensing system of claim 9 which includes a printing device for printing out moisture content information of bales that have been sampled.

11. The moisture sensing system of claim 10 in which said printing device is configured to print a report of moisture of a selected lot of bales.

12. The moisture sensing system of claim 11 in which report lists an average moisture content for each bale in said selected lot of bales.

13. A moisture sensing system for use on a bale lifting vehicle, comprising:

one or more bale penetrating rods mounted to said vehicle, for insertion into a bale of product, with said one or more bale penetrating rods including at least one moisture sensing probe with spaced apart electrodes for moisture sensing contact with a product in bale form;

a sensor readout operatively connected to at least one said moisture sensing probe and mounted on said vehicle in a position visible to a vehicle driver, for displaying moisture readings of product;

an alert set point, and an alarm operatively connected to said moisture sensing probes, wherein a user may select a moisture content as an alert set point, for signaling said vehicle driver if any moisture readings exceed the alert set point;

a memory storage device operatively connected to said moisture sensing probes, in which moisture readings of bales are recorded and saved;

a printing device operatively connected to said memory storage device for printing out moisture content information of bales that have been sampled;

wherein said bale penetrating probes penetrate said bale and take a moisture reading when said bale lifting vehicle moves adjacent a bale, and a driver of said vehicle can read the moisture of said bale while driving said vehicle and print moisture contents of tested bales.

* * * * *